United States Patent [19]

Taniguchi et al.

[11] Patent Number: 5,288,902
[45] Date of Patent: Feb. 22, 1994

[54] METHOD OF MANUFACTURING FERULIC ACID

[75] Inventors: Hisaji Taniguchi; Eisaku Nomura; Takuo Tsuno; Seiko Minami, all of Wakayama; Koji Kato, Hashimoto; Chieko Hayashi, Wakayama, all of Japan

[73] Assignees: Tsuno Food Industrial Co., Ltd.; Wakayama Prefecture, both of Wakayama, Japan

[21] Appl. No.: 845,086

[22] Filed: Mar. 3, 1992

[30] Foreign Application Priority Data

Mar. 13, 1991 [JP] Japan .................. 3-48207

[51] Int. Cl.⁵ .............................. C07C 65/01
[52] U.S. Cl. ................................. 562/478
[58] Field of Search ............................ 562/478

[56] References Cited

U.S. PATENT DOCUMENTS 3,362,892 1/1968 Watanabe .................. 203/89
4,230,817 10/1980 Charbonneau .............. 528/206
4,945,115 7/1990 Liu .......................... 514/731

OTHER PUBLICATIONS

CA91(5):39729y 1978.
J. R. Johnson, Organic Reactions 1, 250 (1942).
Journal of the American Chemical society, 74, 5346 (1952).

*Primary Examiner*—Paul J. Killos
*Attorney, Agent, or Firm*—Nixon & Vanderhye

[57] ABSTRACT

A waste oil, an alkaline oil cake, and a crude fatty acid which are discarded as waste materials or obtained as a by-product in the manufacture of rice salad oil are subjected to hydrolysis in the presence of an alkali so as to efficiently manufacture ferulic acid. The waste materials or by-product accompanying the manufacture of rice salad oil or rice fatty acid, which were disposed of by means of burning in the past, are effectively utilized in the method of the present invention.

11 Claims, 2 Drawing Sheets

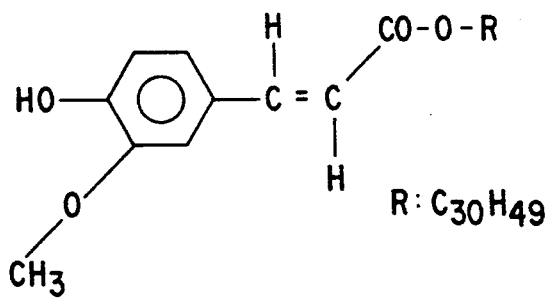
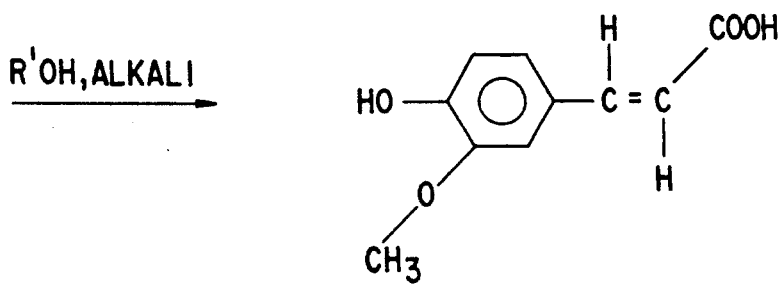
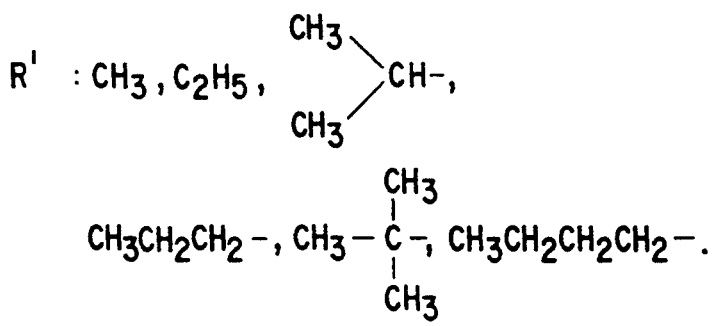
ALKALI: AT LEAST ONE COMPOUND SELECTED FROM THE GROUP CONSISTING OF
NaOH, KOH, $Na_2CO_3$, $K_2CO_3$, $NaHCO_3$, LiOH, AND RuOH

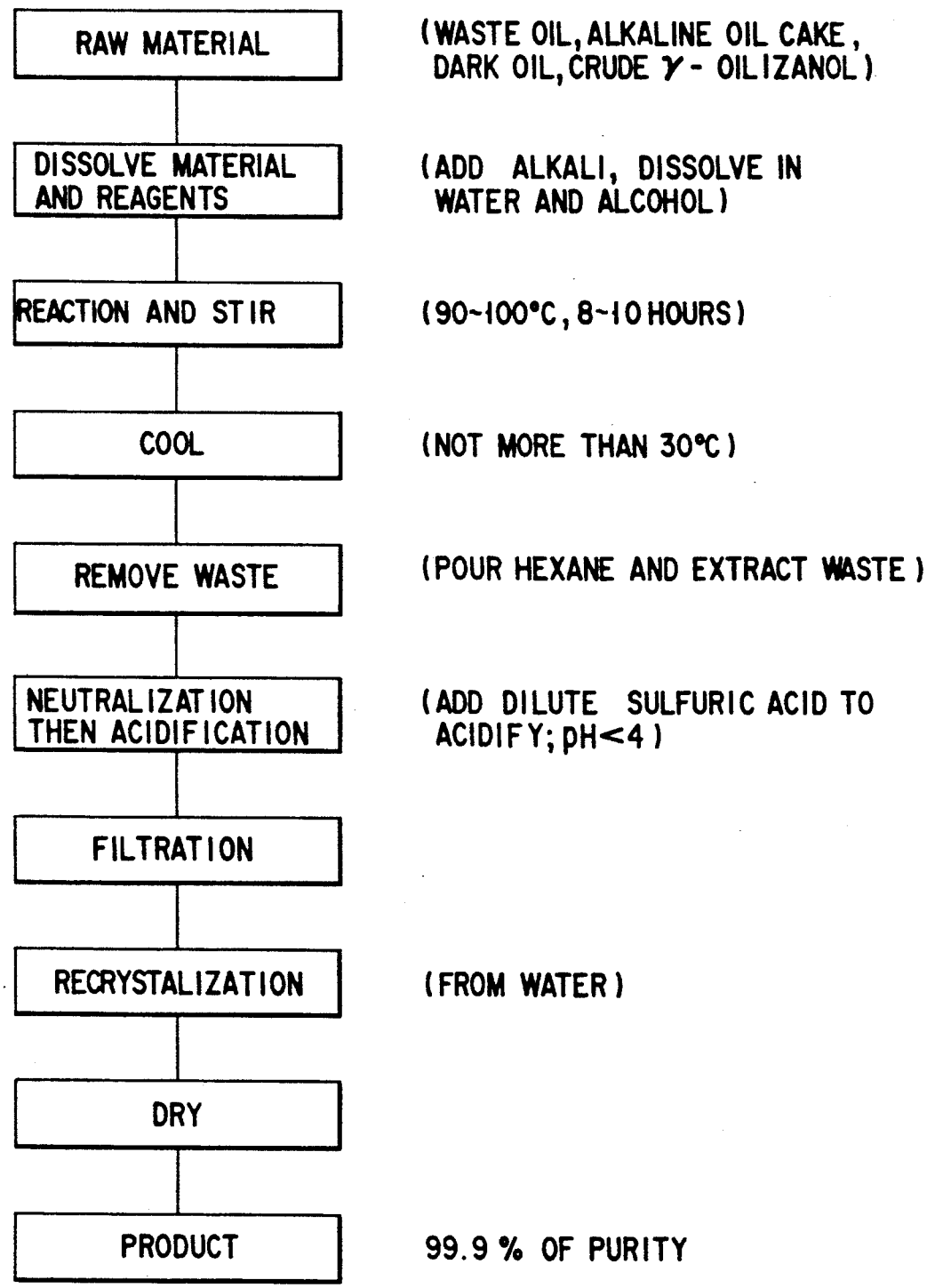

METHOD OF MANUFACTURING FERULIC ACID

BACKGROUND OF THE INVENTION

1. Field of the Invention

The present invention relates to a method of manufacturing ferulic acid which is used as a raw material of, for example, medicines, agricultural chemicals, cosmetics, pigments, and food additives.

2. Description of the Related Art

It is known that ferulic acid is manufactured by the condensation reaction of vanillin with malonic acid, as described in, for example, "Journal of the American Chemical Society, 74, 5346 (1952)". The condensation reaction certainly produces ferulic acid in a high yield. However, it takes as long as about three weeks to manufacture the product ferulic acid, making the known condensation method unsuitable for use in the commercial manufacture of ferulic acid, as described in, for example, "J.R. Johnson, Organic Reactions 1, 250 (1942)". In addition, the product ferulic acid is a mixture of trans- and cis-isomers. Under the circumstances, vigorous researches are being made in this technical field in an attempt to develop a method of manufacturing ferulic acid, which permits commercially manufacturing ferulic acid of high purity, i.e., ferulic acid which does not contain cis-isomer.

In the manufacture of rice salad oil, some by-products and waste materials are discharged, for example, a blackish brown waste oil having a high viscosity, an alkaline oil cake rich in oil components, which is called soap stock, and a by-product rich in crude fatty acids, which is called dark oil. These waste materials and by-products are known to contain useful components. However, it was customary for these waste materials and by-products to be disposed of as useless industrial waste materials by, for example, a burning treatment, because a technique for effectively utilizing these waste materials was unknown in this technical field.

The present inventors have investigated the components of the waste materials and the by-product noted above, and then have found by the chromatographic method that about 10 to 30% by weight of oryzanol is contained in the waste material or the by-product. Certainly, oryzanol itself is a useful component. However, since components other than oryzanol are contained in large amounts in these waste materials or the by-products, it is difficult to recover effectively oryzanol alone, leading to a high manufacturing cost of oryzanol. Thus, it is economically impossible to recover oryzanol from the industrial waste materials or the by-products noted above.

SUMMARY OF THE INVENTION

An object of the present invention is to provide a method of manufacturing ferulic acid by hydrolyzing oryzanol contained in an industrial waste material or a by-product in the presence of an alkali, in place of directly extracting oryzanol from the waste materials or by-products noted above.

Another object is to provide a method of effectively utilizing the waste materials and by-products which are discharged by the manufacture of rice salad oil.

In the method of the present invention, the waste material, by-product or a crude oryzanol is subjected to hydrolysis in the presence of an alkali so as to manufacture ferulic acid. FIG. 1 shows a typical formula of chemical reactions involved in the method of the present invention.

In general, sodium hydroxide or potassium hydroxide is used as an alkali in the step of hydrolyzing oryzanol. It is also possible to use other alkaline compounds such as LiOH, RuOH, $Na_2CO_3$, $K_2CO_3$ and $NaHCO_3$. It should be noted that the waste material or the by-product used as a raw material is quite immiscible with water. Thus, it is desirable to use a suitable alcohol as a solvent in the step of carrying out the hydrolysis in the presence of an alkali. In the case of using a simple alcohol having a small number of carbon atoms, which can be infinitely dissolved in water, the alkaline compound as well as the waste material or by-product in the reaction system can also be dissolved without difficulty.

In carrying out the hydrolysis, it is desirable to set the temperature of the reaction mixture at 90° to 100° C. The reaction time should desirably be 8 to 10 hours. The reaction should desirably be carried out under an atmospheric pressure. Further, the pH of the reaction mixture should desirably be at least 10. A crude ferulic acid having a purity of about 70 to 90% can be obtained as a result of the hydrolysis in the presence of an alkali.

In the next step, a solution containing an alkali salt of ferulic acid is acidified with, for example, a dilute sulfuric acid so as to precipitate ferulic acid in the solution, followed by separating the precipitated ferulic acid by mean of filtration. Heat is generated by the neutralizing reaction in this step. Thus, it is desirable to cool by suitable means the solution containing the alkali salt of ferulic acid so as to maintain the temperature of the solution at 30° C. or less in precipitating ferulic acid. The concentration of sulfuric acid or the like used for the neutralization should desirably be about 10 to 30%. Also, it is desirable to add sulfuric acid or the like such that the solution after the addition of acid should have a pH lower than 4.

The crude ferulic acid separated by filtration is dissolved in hot water (about 90 to 100° C) and, then, the system is cooled so as to permit precipitation of ferulic acid. As a result, obtained is a pure transferulic acid.

The ferulic acid obtained by the method of the present invention can be used as a raw material in the manufacture of, for example, medicines, agricultural chemicals, cosmetics, pigments, and food. Methods of manufacturing these articles from ferulic acid are known to the art. To be more specific, methods of manufacturing cosmetics using ferulic acid as a raw material are described in, for example, Published Unexamined Japanese Patent Application No. 62-120312, Published Unexamined Japanese Patent Application No. 64-13017, and Published Unexamined Japanese Patent Application No. 2-167291. Methods of manufacturing medicines from using ferulic acid as a raw material are described in, for example, Published Unexamined Japanese Patent Application No. 61-204196, Published Unexamined Japanese Patent Application No. 61-204126, Published Unexamined Japanese Patent Application No. 64-13016, and Published Unexamined Japanese Patent Application No. 1-186835. Further, the use of ferulic acid as food additives are described in, for example, Published Unexamined Japanese Patent Application No. 63-283552.

It should be noted in particular that the method of the present invention makes it possible to manufacture ferulic acid useful in the industries from a waste material or a by-product which is discharged by the manufacture of rice salad oil.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention and, together with the general description given above and the detailed description of the preferred embodiments given below, serve to explain the principles of the invention.

FIG. 1 exemplifies a typical chemical formula of reactions utilized in the method of the present invention; and FIG. 2 schematically shows the typical steps included in the method of the present invention.

DETAILED DESCRIPTION OF THE PREFERRED EMBODIMENTS

Let us describe some examples of the present invention.

EXAMPLE 1

10 g of a blackish brown waste oil called pitch, which is discharged as a by-product in producing a rice fatty oil from rice bran, was put in a three-necked flask. Then, 5g of sodium hydroxide, 20 ml of water and 20 ml of isopropyl alcohol were added to the waste oil. The mixture in the system was heated to 90° to 100° C. until the mixture was boiled, and was stirred for about 8 hours at that temperature. The reaction was carried out for 8 to 10 hours at 90° to 100° C. under an atmospheric pressure (1 atm.). After the reaction, the reaction system was cooled, followed by pouring hexane into the reaction mixture so as to remove the materials soluble in hexane. Then, a dilute sulfuric acid was added to the aqueous solution after removal of the materials soluble in hexane so as to acidify the aqueous solution and, thus, to precipitate ferulic acid. The temperature at which ferulic acid was deposited was 30° C. or less, the concentration of the dilute sulfuric acid was 10 to 30%, and the pH of the aqueous solution was 1 to 4. The aqueous solution containing the precipitated ferulic acid was filtered so as to obtain 1.2g of crude ferulic acid having a purity of 80%. The crude ferulic acid thus obtained was dissolved in hot water of 90° to 100° C., followed by cooling the resultant solution for recrystallization, thereby obtaining pure trans-ferulic acid. The chemical structure of the product trans-ferulic acid was confirmed by the measurement with NMR spectrum and infrared ray spectrum. The trans-ferulic acid thus obtained was found to have a melting point of 174° C. The yield of ferulic acid based on the raw material waste oil was 9.6% by weight and the molar yield of ferulic acid based on oryzanol was 100%. Further, the purity of the product ferulic acid was found to be 99.9%.

EXAMPLE 2

Operations as in Example 1 were carried out, except that 5g of potassium hydroxide was used in place of sodium hydroxide used in Example 1. Obtained was 1.0g of crude ferulic acid. The yield of ferulic acid based on the raw material waste oil was 8% by weight and the molar yield of ferulic acid based on oryzanol was 83%. Further, the purity of the product ferulic acid was found to be 99.9%.

EXAMPLE 3

Operations as in Example 1 were carried out, except that 10g of an alkaline oil cake rich in oil components, which is called soap stock, was used in place of the blackish brown waste oil used in Example 1. Obtained was 0.2g of crude ferulic acid. The yield of ferulic acid based on the raw material alkaline oil cake was 2% by weight. Further, the purity of the product ferulic acid was found to be 99.9%.

EXAMPLE 4

Operations as in Example 1 were carried out, except that 10 g of a by-product called dark oil, which is rich in crude fatty acid, was used in place of the blackish brown waste oil used in Example 1. Obtained was 0.3g of crude ferulic acid. The yield of ferulic acid based on the raw material dark oil was 3% by weight. Further, the purity of the product ferulic acid was found to be 99.9%.

EXAMPLE 5

Operations as in Example 1 were carried out, except that 10g of a crude oryzanol available on the market and having a purity of about 80% was used in place of the blackish brown waste oil used in Example 1. Obtained was 2.2g of crude ferulic acid. The yield of ferulic acid based on the raw material crude oryzanol was 17 to 18% by weight, and the molar yield of the product ferulic acid based on oryzanol was 86%. Further, the purity of the product ferulic acid was found to be 99.9%.

The reaction conditions in the hydrolyzing step and the conditions of precipitate of ferulic a id in each of Examples 2 to 5 were equal to those in Example 1.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. A method of manufacturing ferulic acid, comprising the steps of:
   preparing a raw material containing γ-oryzanol, said raw material selected from the group consisting of a waste material, a by-product, and a mixture of said waste material and by-product accompanying the manufacture of rice salad oil or rice fatty acid from rice bran; and
   subjecting the γ-oryzanol-containing raw material to hydrolysis in the presence of an alkali including the steps of:
   (a) mixing the raw material with an alkali and stirring the resultant mixture while heating;
   (b) cooling the reaction mixture obtained in step (1);
   (c) pouring an organic solvent into the cooled reaction mixture so as to remove the materials soluble in said organic solvent and removing the organic solvent leaving an aqueous solution.
   (d) acidifying the aqueous solution obtained after removal of the materials soluble in the organic solvent so as to precipitate ferulic acid; and thereafter (e) removing the precipitated ferulic acid, dissolving it in water and recrystallizing ferulic acid.

2. The method according to claim 1, wherein said raw material is a waste oil accompanying the manufacture of rice fatty acid from rice bran.

3. The method according to claim 1, wherein said raw material is an alkaline oil cake accompanying the manufacture of rice salad oil from rice bran.

4. The method according to claim 1, wherein said raw material is a crude fatty oil accompanying the manufacture of rice salad oil from rice bran.

5. The method according to claim 1, wherein said alkali used in the hydrolysis step is selected from the group consisting of sodium hydroxide, potassium hydroxide, LiOH, RuOH, $Na_2CO_3$, $K_2CO_3$, $NaHCO_3$, and a mixture thereof.

6. The method according to claim 5, wherein said alkali used in the hydrolysis step is selected from the group consisting of sodium hydroxide, potassium hydroxide, and a mixture thereof.

7. The method according to claim 1, wherein said hydrolysis is carried out by dissolving the raw material in an alcohol solvent.

8. The method according to claim 7, wherein said alcohol solvent is formed of at least one compound selected from the group consisting of the compounds represented by chemical formulas given below:

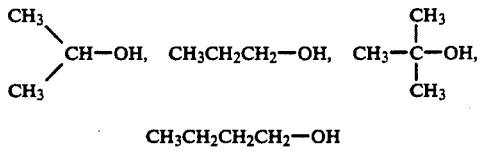

9. The method according to claim 1, wherein a crude ferulic acid having a purity of 70 to 90% is obtained by the hydrolysis performed in the presence of an alkali.

10. The method according to claim 1, wherein said water for dissolving the ferulic acid separated by filtration has a temperature of 90° to 100° C.

11. The method according to claim 1, wherein said ferulic acid is trans-ferulic acid.

* * * * *